United States Patent [19]
Knollenberg et al.

[11] Patent Number: 5,493,123
[45] Date of Patent: Feb. 20, 1996

[54] SURFACE DEFECT INSPECTION SYSTEM AND METHOD

[75] Inventors: Robert G. Knollenberg, Boulder; Vaughn C. Hoxie, Longmont; Clinton E. Utter, Aurora, all of Colo.

[73] Assignee: Particle Measuring Systems, Inc., Boulder, Colo.

[21] Appl. No.: 234,402

[22] Filed: Apr. 28, 1994

[51] Int. Cl.⁶ .......................... G01N 21/47; G01N 21/88
[52] U.S. Cl. .......................... 250/372; 250/358.1; 356/237
[58] Field of Search .................... 250/372, 358.1, 250/359.1, 360.1, 572; 356/237

[56] References Cited

U.S. PATENT DOCUMENTS

| | | | |
|---|---|---|---|
| 4,314,763 | 2/1982 | Steigmeier et al. | 356/237 |
| 4,598,997 | 7/1986 | Steigmeier et al. | 356/237 |
| 4,659,933 | 4/1987 | Anthon | 250/358.1 X |
| 4,798,465 | 1/1989 | Knollenberg . | |
| 4,893,928 | 1/1990 | Knollenberg . | |
| 4,893,932 | 1/1990 | Knollenberg . | |
| 5,264,912 | 11/1993 | Vaught et al. | 356/237 |
| 5,282,151 | 1/1994 | Knollenberg . | |

FOREIGN PATENT DOCUMENTS

| | | | |
|---|---|---|---|
| 53-72679 | 6/1978 | Japan | 356/237 |
| 60-169743 | 9/1985 | Japan | 250/372 |

OTHER PUBLICATIONS

"The Importance of Media Refractivr Index in Evaluating Liquid and Surface Microcontamination Measurements" By Dr. Robert G. Knollenberg In Proceedings—Institute of Environmental Sciences (No Date).

"A Polarization Diversity Two–Color Surface Analysis System" By Robert G. Knollenberg In Proceeding—Institute of Environmental Sciences (No Date).

*Primary Examiner*—Carolyn E. Fields
*Assistant Examiner*—Edward J. Glick
*Attorney, Agent, or Firm*—Robert E. Harris

[57] ABSTRACT

System and method are disclosed for inspecting objects, such as sheets of flat panel glass, to detect flaws or contamination at a surface. The surface to be inspected is illuminated with 253.7 nm ultraviolet (UV) radiation to assure detection of defects only at the front surface subjected to the radiation. UV radiation reaching the front surface is scattered by defects at the front surface, and scattered UV radiation is collected by a UV dark field imaging system and directed by the imaging system to a detecting unit, preferably including a charge coupled device (CCD). The detecting unit senses UV radiation scattered at the surface due to defects within a selected size range and provides an output to a processing unit providing an output indicative of the defects sensed within the selected size range. The illumination system preferably illuminates the entire surface to be inspected, an enclosed dark field chamber having shielding houses the illuminating source and radiation collecting system, an anti-reflecting UV coating is preferably used, as is a bandpass filter, and the detecting unit is preferably cooled, accompanied by heating of the imaging system. The system is capable of detecting defects at least as small as five microns using a ten second sampling period.

28 Claims, 4 Drawing Sheets

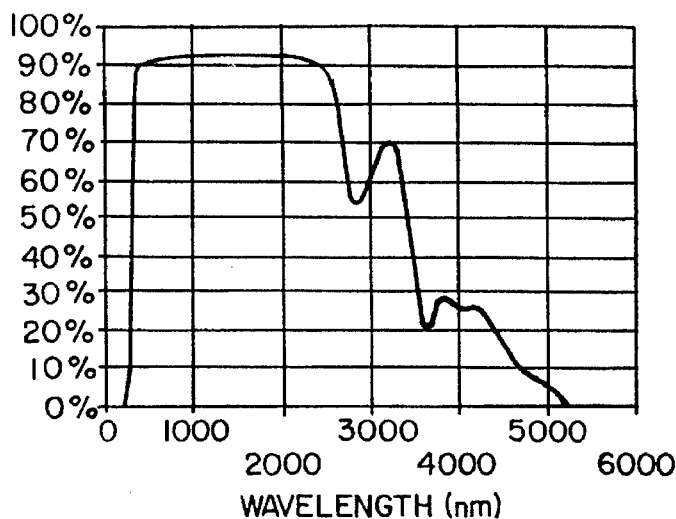
Fig_1A
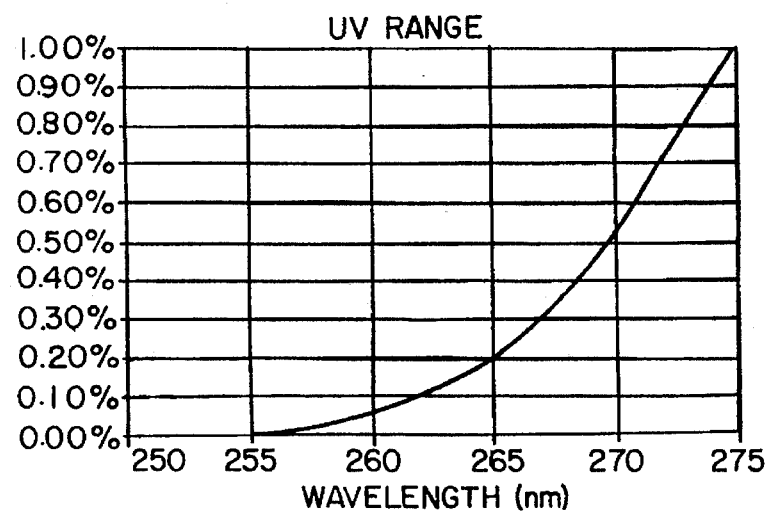
Fig_1B
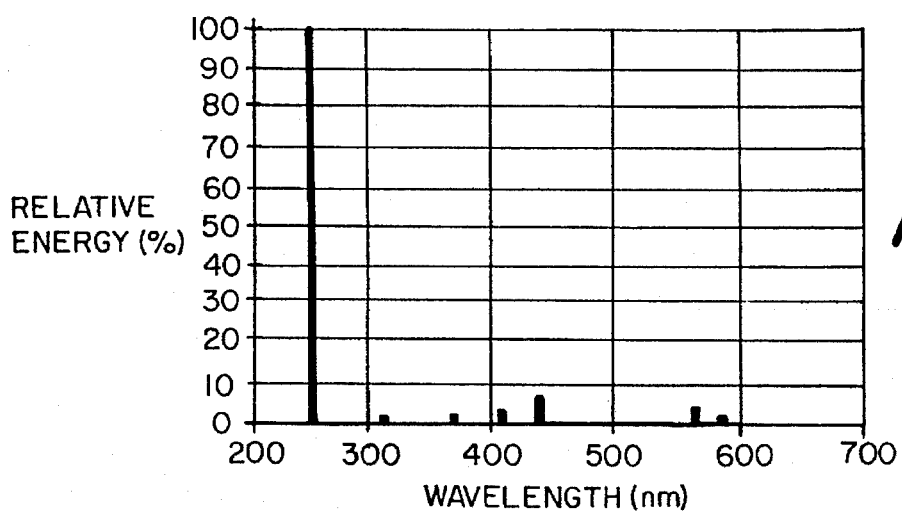
Fig_2

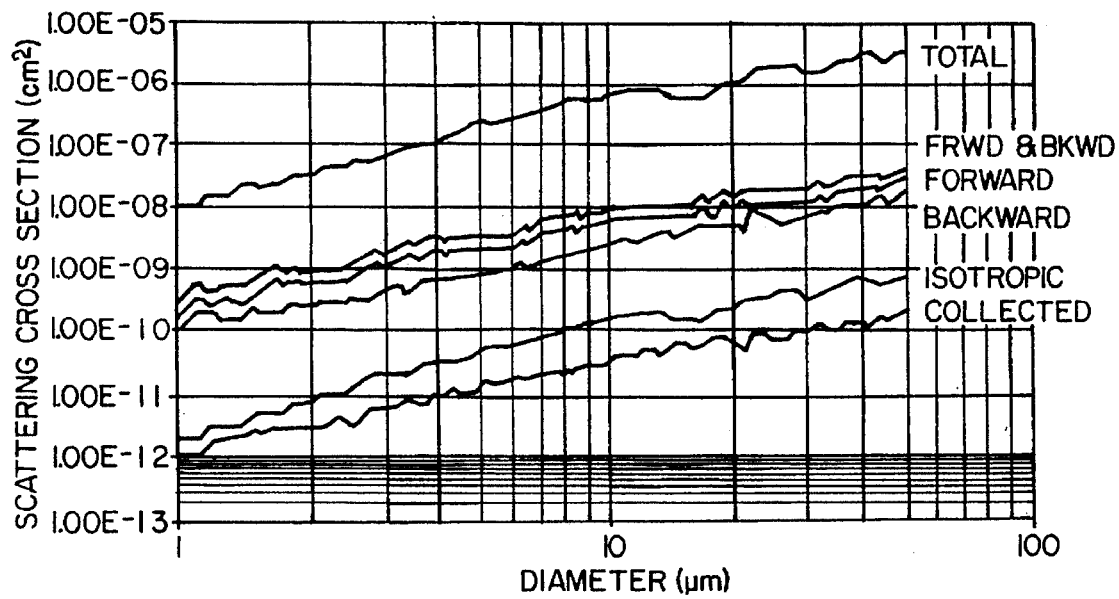
Fig_3
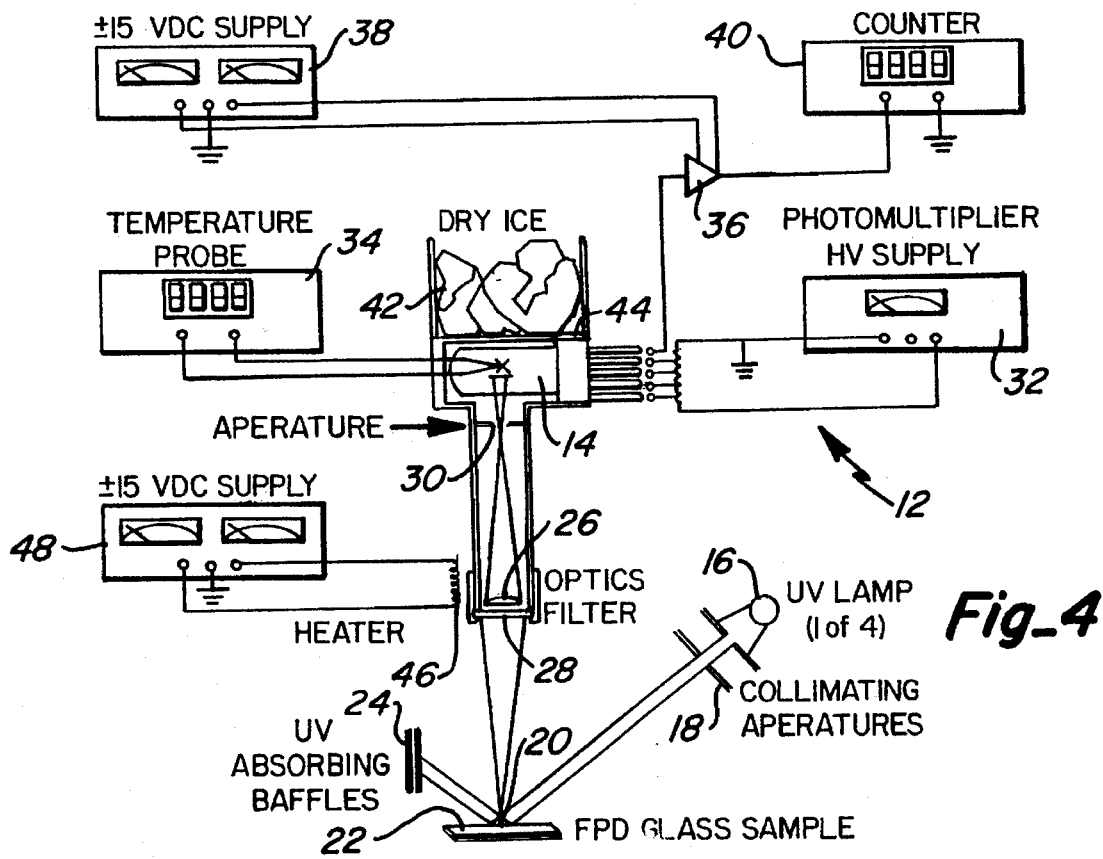
Fig_4

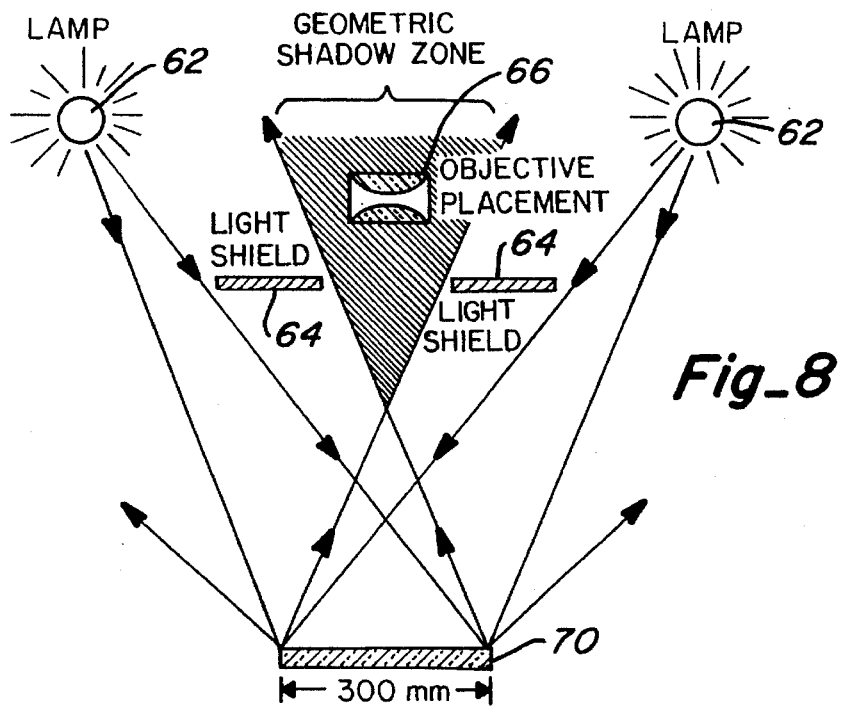
Fig_8
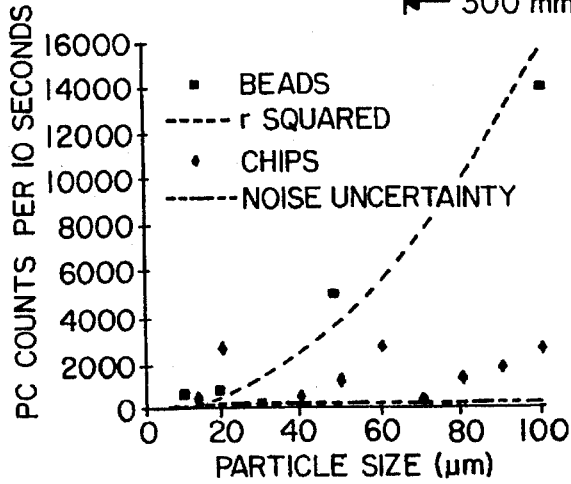
Fig_5
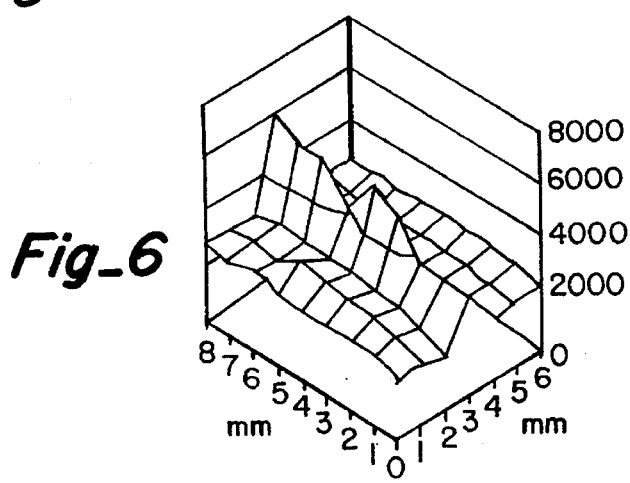
Fig_6

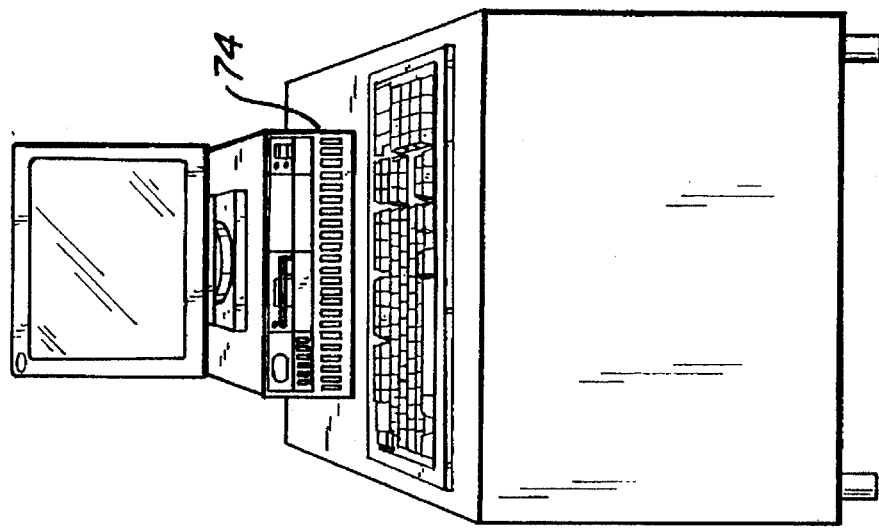
Fig_9
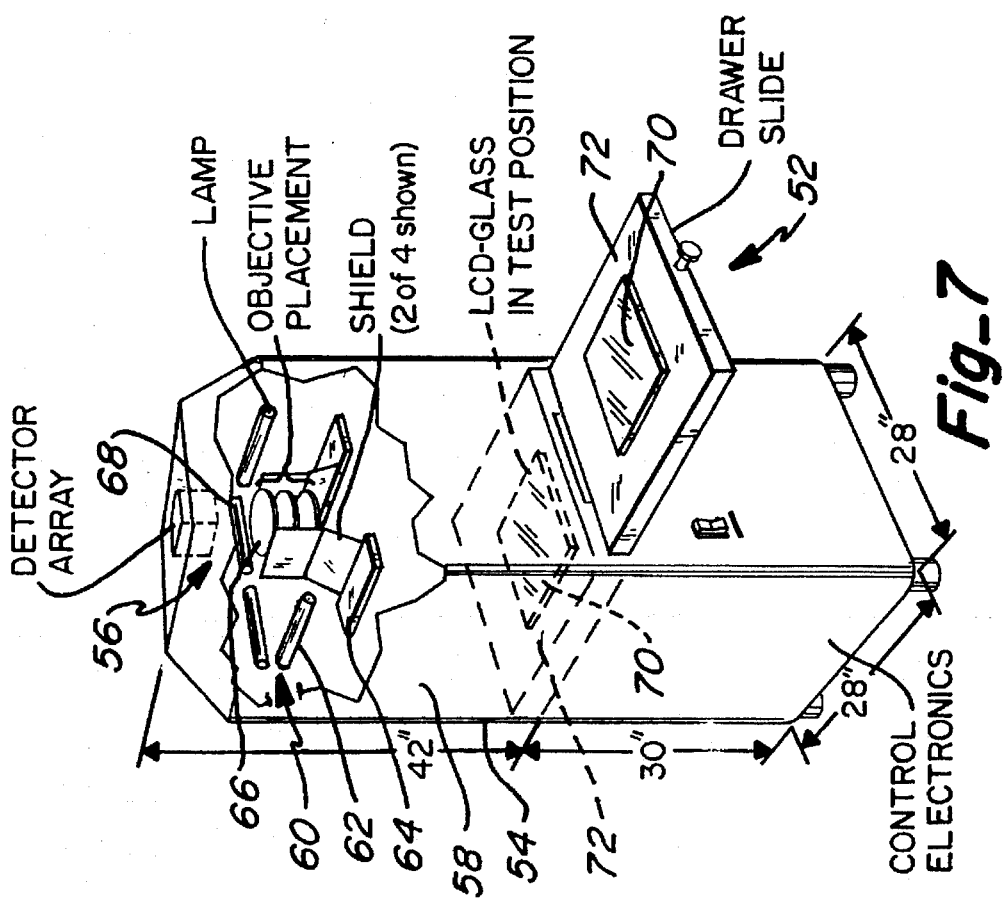
Fig_7

SURFACE DEFECT INSPECTION SYSTEM AND METHOD

FIELD OF THE INVENTION

This invention relates to a surface defect inspection system and method, and more particularly, relates to an inspection system and method for detecting surface defects in a sheet of flat panel glass.

BACKGROUND OF THE INVENTION

Testing of objects to detect surface flaws or defects is now known in connection with diverse units, as is testing for conditions leading to, or causing, contamination of surfaces.

Contamination control is important, for example, in integrated circuit fabrication, as is a determination of defects or contaminated areas in wafer substrates. While control of contaminated areas in an overall object can often be readily achieved by eliminating the contaminated areas, many objects do not lend themselves to such readily achieved correction, and this is particularly true, for example, in the case of flat panel displays where cutting out contaminated areas from the entire display is normally impossible. It has therefore become increasingly necessary to be able to determine the presence of defects or surface contamination, particularly where such defects are present at a surface of an object, for example, at the front, or quality, surface of sheets of flat glass.

Detection of defects at a surface is known utilizing a laser to illuminate the surface (see, for example, U.S. Pat. No. 4,893,932), as is the use of a charge coupled device (CCD) to detect sub-micron particles causing scattering of light from a laser (see, for example, U.S. Pat. No. 5,282,151).

In the case of flat glass displays, however, glass sheet inspection now normally involves visual examination under controlled lighting conditions with defect qualification done either by comparing the sample to a uniform standard or by determining the threshold of detection by varying the illumination level. Thus, current inspection has the inherent subjectivity of human inspection as well as requiring significant product handling, and, if quantitative data is desired for statistical quality control, the location of defects and preservation of such data must often be additionally obtained and preserved.

Automated inspection of flat panel display glass has met limited success, due, at least in part, to long inspection times, lack of size resolution, and susceptibility to optical noise from both the environment and the substrate itself.

It is therefore evident that improved systems and methods are needed for determining defects at the surface of objects, and, particularly, in determining defects at a surface of a sheet of flat glass.

SUMMARY OF THE INVENTION

This invention provides improved system and method for determining defects at the surface of objects, and, particularly, in determining defects at a surface of flat glass, including providing good size resolution within an acceptable sampling, or inspection, time period.

The surface to be inspected is illuminated with radiation, preferably ultraviolet (UV) radiation at 253.7 nm, illuminating the entire surface to be inspected, to achieve detection of defects only at the first surface of an object receiving the radiation, with defects at the surface scattering the radiation. The scattered radiation is collected by an imaging system, preferably a UV dark field imaging system, and the collected radiation is directed to a detecting unit, preferably including a charge coupling device (CCD), where the scattered radiation due to defects within a predetermined size range is detected and processed to provide an output indicative of the defects sensed within the predetermined range, preferably having a minimum size at least as small as five microns with a ten second defect sampling period.

It is therefore an object of this invention to provide an improved system and method for determining surface defects.

It is another object of this invention to provide an improved system and method for determining defects at a glass surface.

It is yet another object of this invention to provide an improved system and method for determining defects at the front surface of a sheet of flat panel glass.

It is still another object of this invention to provide an improved system and method that includes illuminating the entire surface to be inspected with radiation, detecting radiation scattered by defects at the surface, and processing the detected radiation to provide an output indicative of defects sensed by the detecting means within a predetermined size range.

It is yet another object of this invention to provide an improved system and method that includes illuminating a surface with radiation, preferably UV radiation at 253.7 nm, detecting the radiation scattered by defects at the surface within a predetermined size range and preferably at least as small as five microns, and processing the detected signal to provide an output indicative of defects sensed by the detecting means within the predetermined size range.

With these and other objects in view, which will become apparent to one skilled in the art as the description proceeds, this invention resides in the novel construction, combination, arrangement of parts and method substantially as hereinafter described, and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate complete embodiments of the invention according to the best mode so far devised for the practical application of the principles thereof, and in which:

FIGS. 1A and 1B are graphs illustrating flat glass transmittance for 0.7 mm glass thickness;

FIG. 2 is a graph illustrating UV source spectral energy distribution;

FIG. 3 is a graph illustrating computed particle scattering cross sections;

FIG. 4 is a simplified schematic diagram of a prototype system according to this invention;

FIG. 5 is a graph illustrating sizing response for soda lime glass beads using the system of FIG. 4;

FIG. 6 is a topographic plot illustrating a scratch profile;

FIG. 7 is a perspective view of the system of this invention;

FIG. 8 is a simplified sketch illustrating dark field imaging for the system shown in FIG. 7; and FIG. 9 is a front view illustrating a data processor computer usable as a part of the overall system of this invention.

DESCRIPTION OF THE INVENTION

A fundamental challenge in a system for detection of defects utilizing light scattering is to separate the signal of the defect from background noise sources, and, where surface defects or contamination are to be detected, it is also necessary to separate the signal of the defect from that of surface sources. For a glass inspection system, there is still an additional challenge in differentiating the front or quality surface contamination from backside contamination and internal defects, such as, for example, inclusions, seeds and bubbles.

While consideration was given to several possible approaches in view of the foregoing, including the use of infrared and visible wavelengths for illuminating the surface area to be inspected, high magnification detection, and/or scanning of the area to be inspected by sweeping a spot across the surface, the use of ultraviolet (UV) illumination appeared to be, and is now, the preferred source of illumination for detecting only front surface defects, with the illumination preferably fully illuminating the surface to be inspected and imaging the illuminated surface onto a large area detector, as brought out in greater detail hereinafter.

FIGS. 1A and 1B illustrate typical transmittance of flat panel glass. FIG. 1A shows a transmission band from under 300 nm to over 5000 nm, and indicates infrared transmittance to be quite substantial even at 5000 nm. FIG. 1B shows the UV range and illustrates a hard cutoff in the UV shortward of 260 nm, with detailed analysis yielding a transmission of ~0.045% at 253.7 nm. With a worst case assumption of 0.10% for a 0.7 mm thickness, a 253.7 nm signal received from backside defects would decrease to $(0.001)^2$ or one part per million (ppm) which is negligible.

Theoretical calculations indicated that through the use of a dark field illumination system and an array of detectors (preferably a charge coupled device (CCD)) covering a large area, it would be possible to image onto each detector (i.e., onto each pixel of a CCD) a sufficiently small surface area to reduce the collected surface induced scatter below the scattering signal from five microns and smaller surface defects.

Samples of flat panel glass of the type to be inspected by the system and method of this invention showed, before wet cleaning, RMS roughness of 3.9 Å with several point defects having excessive heights. After wet cleaning, the overall RMS roughness was reduced to 1.6 Å. The total integration scatter (TIS) from a surface is related to RMS roughness height (h) and wavelength ($\lambda$), and, more particularly, is equal to the square of $4\pi h$ divided by $\lambda$.

With values of h ranging from 1.6 Å to 3.9 Å and yielding estimated values from 60 ppm to 400 ppm at 253.7 nm, unclean surfaces with 400 ppm TIS would limit sensitivity, but, with cleaning, an assumption of 100 ppm appeared reasonable for theoretical calculations (realizing that for unclean glass, a higher detector threshold, such as ten or fifteen microns, for example, might need to be utilized).

The amount of signal generated by the surface or particles on the surface can be estimated from a knowledge of the illumination energy density, scattering characteristics, optical collection efficiency and detector responsivity. Since CCD's are normally characterized in terms of collected electrons ($e^-$) and quantum efficiency ($e^-$/photon), discussion is simplified by converting illumination energy density into photons $cm^{-2}$ $sec^{-1}$ and limit computations to photons, electrons and photo-electrons ($pe^-$).

Using a plurality of low pressure mercury lamps (sometimes known as germicidal lamps or Koller germicidal lamps) with a dominant line at 253.7 nm, the source lamps produce an illumination energy density ranging from 100–1100 mW $cm^{-2}$ at 25 cm. Using G25T8 lamps (General Electric) which produce a nominal 800 mW $cm^{-2}$ at 25 cm, and with illumination varying as $1/r^2$ at 75 cm, ~90 mW $cm^{-2}$ of UV illumination can be expected to reach the surface to be inspected from each lamp used. FIG. 2 shows the spectral energy distribution of this series of lamps Using four of these lamps, 350 mW $cm^{-2}$ or a corresponding flux of ~$4.2 \times 10^{14}$ photons $cm^{-2}$ $sec^{-1}$ will be realized.

Evaluation of the optical system performance was made in view of specified physical dimensions and properties, as brought out hereinafter. The optical system includes a four element fused silica lens assembly. With an objective diameter of 5 cm, the system has a numerical aperture of ~0.3, and provides the necessary flat focal plane. With an aperture stop of ~1.5 cm, there is a collection angle of 1.2° with a collection efficiency of 0.005%. The optical elements will have a combined transmittance of ~86%. To eliminate ambient light and the Hg emission lines of the source, the system includes a 10 nm bandpass filter, which has a peak transmittance at 254 nm of 17% and falls to less than $10^{-4}$ by 350 nm. The total optics design provides an off-axis point resolution of <15 microns. The object field of view of each CCD element will be ~375 microns on a side or 140,000 $\mu m^2$ (microns squared) total. The CCD sensor has an anti-reflection coating improving quantum efficiency to ~12% at 253.7 nm. Additionally, photon collection is integrated for ten seconds per sample.

With a point resolution of <15 microns, a point defect will fall completely onto one CCD element only if it is exactly centered in the viewed area, otherwise it will be spread across up to four contiguous elements. Therefore, looking at any four contiguous viewed areas with 100 ppm TIS each, there is an equivalent of 56 $\mu m^2$ of TIS cross section which, with the given incident photon flux, generates a (TIS) photon flux of $2.4 \times 10^2$ photons $sec^{-1}$.

With the given collection efficiency, there is a collected TIS of $1.3 \times 10^4$ photons $sec^{-1}$ and, with the combined optical efficiencies, the TIS generated UV photon flux at the detector is ~1900 photons $sec^{-1}$. With a detector conversion efficiency of 12%, a total $pe^-$ rate is obtained from the four CCD elements of 228 $pe^-$ $sec^{-1}$, or 2280 $e^-$ after a ten second integration. This rate has an RMS uncertainty of $\sqrt{2280}$ or 48 $pe^-$.

Since glass is not highly reflective, scattering due to particles on the surface is not vastly different from the scattering of particles suspended in air. However, an optical system viewing particles from above sees light both directly scattered from the particle as well as light which may reflect off the surface prior to illuminating the particle. Since the surface reflectivity is ~4% for flat panel glass, contributions reflected from the surface are ordinarily small except when scattering angles involved are quite low. FIG. 3 illustrates the pertinent MIE scattering cross sections for diameters of particles with a refractive index of 1.77 (the refractive index of calibration latex monospheres at 253.7 nm). As can be observed in FIG. 3, the total scattering cross-section (top curve of FIG. 3) approaches twice the physical cross-sectional area of the particle. The collection optics required to view the entire glass sheet are obviously sufficiently small in diameter and far enough removed from the surface to only collect a fraction of a percent of the total light scattered, while the camera lens will collect backscatter from 160°–175° and forward scatter from 5°–20° due to the extended sources used (curves 2, 3 and 4, in descending order, of FIG. 3). The theoretical scattering cross section, as realized by the optical system collecting scattering energies over these angles is shown in the bottom curve of FIG. 3. The second from the bottom curve of FIG. 3 illustrates the expected curve for an instrument cross section if the particles scattered isotropically.

From the curves illustrated in FIG. 3, it is found that, at a given diameter of ten microns, there is an instrumental scattering cross section of $9.4 \times 10^{-11}$ cm$^{-2}$ which, when multiplied by the incident photon flux of $4.2 \times 10^{14}$ photons cm$^{-2}$ sec$^{-1}$ generates a collected particle photon flux of $3.9 \times 10^4$ photons sec$^{-1}$. With losses through the optics this is reduced to 5500 photons sec$^{-1}$ at the detector and 670 pe$^-$ sec$^{-1}$ from the detector. After ten seconds of integration, a particle of the size of interest generates a total of 6700 e$^-$ with a signal-to-noise ratio over the TIS uncertainty of 6700/48= 143:1. A similar calculation shows that a five micron particle would generate ~2000 pe$^-$ after ten seconds and would have a S/N ratio of 44:1. Following this type of calculation back, it is found that the full well capacity of 150,000 pe$^-$ for each CCD element yields a maximum resolvable size of ~120 microns.

Based upon the foregoing, a preliminary system 12, as shown in FIG. 4, with a scaled single element detector 14, verifies and illustrates the invention. To best match the characteristics of a CCD, a UV responsive photo-multiplier tube (PMT) was selected as single element detector 14. With the PMT operated in a photon counting mode, it is rather straight forward to correlate the PMT response to that of a CCD. The PMT has a 13% conversion efficiency at 253 nm, which is very similar to that of the CCD, with thermally induced noise counts of ~300 cts/sec at 20° C., dropping to <10 cts/sec at –40° C. The CCD's published noise figures show <10 cts/sec for the standard operating mode at –40° C. and <1 cts/sec when operated with special clocking techniques.

As shown in FIG. 4, radiation from UV lamp 16 (one of four G8T5 lamps utilized) is directed through collimating apertures 18 to front, or first, surface 20 of a glass sheet 22 then to be inspected to illuminate the surface then to be inspected. The G8T5 lamps are smaller, low wattage versions of the G25T8 lamps referred to above, and four of these lamps at 180 mm, provided an illumination level of ~340 mW cm$^{-2}$ giving a UV photon flux of $4.3 \times 10^{14}$ photons cm$^{-2}$ sec$^{-1}$.

As indicated, UV absorbing baffles 24 collect the reflected radiation not scattered by particles at surface 20. Baffles 24 are UV absorbing panels used to line the sample chamber, and baffles 24, in conjunction with collimating apertures 18, maintain the dark field around the objective. This setup provided a dark chamber count of 200–500 cts/10 sec and an illuminated but empty test chamber count of 500–800 cts/10 sec.

Radiation scattered by defects or particles at surface 20 are collected by imaging unit 26 through bandpass filter 28. The optical elements are standard, uncoated fused silica, 15 mm in diameter. Radiation collected by imaging unit 26 is directed, or imaged, through aperture 30 onto PMT detector 14 (as indicated, PMT detector 14 is powered by photo multiplier high voltage power supply 32, and has temperature probe 34 connected therewith). For simplicity of design and because of the size of the optics, the objective distance was kept short (about 130 mm). The smaller optics at a closer distance yielded a 2.8° collection angle with 0.015% collection efficiency.

The output from PMT detector 14 is coupled through amplifier 36 (powered by fifteen volt power supply 38) to counter 40.

To cool detector 14 and reduce the thermal noise counts to a minimum, a reservoir 42 of dry ice is positioned over housing 44 of detector 14. It has been found that the detector temperature can be held to –20° C. with thermally induced counts of ~50 sec$^{-1}$. Where needed to prevent the optics from frosting, small strip heater 46 may be positioned adjacent to the optics, with strip heater 46 powered by fifteen volt power supply 48.

Using the system shown in FIG. 4, a large number of glass samples were scanned and TIS values were found in the 1500–2500 cts/10 sec range, varying from sample to sample as well as across individual samples. To establish a sizing response, several calibration soda lime glass beads were also scanned. The smallest clearly resolvable bead had a diameter of eleven microns giving a differential count of 450 cts/10 sec. Additional data was gathered on a number of known size defects, and this data is set forth in FIG. 5. The glass beads very nearly followed the anticipated r$^2$ response, as did the smaller chips, while the larger chips tended to oversize, most likely due to the larger chips lying flat and presenting their largest aspect ratio during inspection.

The signals received during the above testing were smaller than expected, due, in part, to the effect of the collimating apertures on the flux for the lamps, for which there was not a good estimate available. Deviation from predicted signal-to-noise ratios is attributed to a combination of factors, including excessive circulating stray light in the test chamber, a different index of refraction of the glass beads (1.53 at 254 nm) from that of the modeled Polystyrene latex (PSL) monospheres, and potential variations of the TIS scattering response at the UV wavelengths used. Projecting the theoretical response down to the limit of resolution, a 3:1 S/N ratio was calculated for a five micron particle. The smallest size detected, however, by the system of FIG. 4 was a six micron particle at ~2:1 S/N ratio. By reducing the effective area viewed per pixel, as brought out hereinafter, the detection threshold is to be reduced to at least five microns, and perhaps to near two microns.

Sensitivity to scratches was also confirmed using the system of FIG. 3. Since scratches are extended features, it was felt that they would be detectable, but there was no model that allowed an estimation of the level of sensitivity. FIG. 6 sets forth a topographical representation of data from a 5 kLux scratch, extending over more than 8 mm, and shows clearly the relative levels of defect to surface signal. Additional scans with the scratch rotated at 45° and 90° showed no significant differences, indicating little orientation bias.

Using preliminary system 12 as a basis, inspection system 52, as shown in FIG. 7, was developed to operate essentially in the same manner as does preliminary system 12, but achieve better defect size resolutions. As shown in FIG. 7, a Cluster island frame 54 houses the various components of system 52. With optical detection unit 56 housed in sealed enclosure 58, with the inspection apparatus having no moving parts, and with allowance for installing a HEPA filter atop enclosure 58, a very low level of self contamination is ensured.

Illumination unit 60 is also within sealed enclosure 58, and this unit includes an array of four G25T8 germicidal lamps 62. Each of these lamps produces 5 Watts of radiant power at 253.7 nm, and each lamp is monitored by a UV sensitive photo-detector located at the lamp. The illumination system is baffled, including through use of shields 64, using anti-reflection coated, UV absorbing material, to maintain a very black environment in the UV range, preserve the dark field around collection optics unit 66, and reduce circulating stray light (as indicated by the simplified sketch of FIG. 8).

Optical detection unit 56 includes both collection optics unit 66 and detector unit 68. Optics unit 66 has UV transparent collection optics with the optical elements coated to minimize reflections and to eliminate the influence of the extraneous Hg lines from the UV illuminating lamps, and the lens system images a 15"× 19" sheet of flat plate glass onto detector unit 68 (and hence onto a CCD when included in detector unit 68) with ~375 µm resolution per CCD element. Detector unit 68 is preferably a UV enhanced CCD array, and, more particularly, could be, for example, a 1024×1280 UV enhanced, thermo-electrically cooled, CCD array.

As shown in FIG. 7, during operation each sample 70 is manually positioned at the inspection area by drawer slide 72 (as shown by dotted lines in FIG. 7). It is to be realized, however, that automatic positioning could be utilized, including coordinated positioning during glass handling operations, without departing from the intended scope of this invention.

In operation, the system and method described herein contemplates use of ten seconds of photon collection per sample. If requirements (such as production requirements) allow more relaxed sensitivity, integration times could be shortened (and thus provide improved production throughput). The entire contents of the CCD array can be downloaded to a data processor (such as, for example, to data processor computer 74 as shown in FIG. 9) in less than three seconds (and faster if some noise degradation is allowable).

Data processor computer 74 provides the interface necessary to control the CCD detector unit and the data collection channel, as well as providing straight forward access to data processing parameters, size threshold information, and data storage abilities. The CCD video image is preferably collected by a high speed, digital signal processor, frame grabber card which applies the needed normalization and spatial filters to the entire video frame in ~4 seconds, and can perform thresholding and gray level histograms in under one second each. The total product cycle time takes 30 seconds, with ten seconds for product loading, ten seconds for image collection, and the final ten seconds for product unloading and data processing, at the end of which, inspection information will be available. Data presentation can be provided in a number of ways, including, for example, through use of a color monitor to display a color coded defect map with precise X—Y defect locations depicted thereon.

As can be appreciated from the foregoing, this invention provides an improved system and method for detecting defects on a surface, and , more particularly in detecting defects on the front surface of a sheet of flat glass.

What is claimed is:

1. A surface defect inspection system, comprising:

illuminating means providing ultraviolet radiation during a predetermined inspection period;

positioning means for positioning glass sheet having a surface to be inspected so that all areas of said surface to be inspected are completely illuminated during the entirety of said inspection period by said ultraviolet radiation from said illuminating means whereby defects at each said area of said illuminated surface will cause scattering of said ultraviolet radiation during said inspection period;

detecting means having a sufficiently large detecting area for separate simultaneous sensing of ultraviolet radiation scattered at said areas of said illuminated surface during inspection due to defects at each of said areas of said illuminate surface that are within a predetermined size range and providing an output indicative of each sensed defect; and processing means for receiving said output from said detecting means and, responsive thereto, providing an output indicative of each defect sensed at said areas of said surface that is within said predetermined size range.

2. The system of claim 1 wherein said illuminating means provides ultraviolet radiation shortward of 260 nm.

3. The system of claim 1 wherein said illuminating means includes a plurality of low pressure mercury lamps for illuminating said surface to be inspected.

4. The system of claim 1 wherein said object to be inspected is a sheet of flat panel glass, and wherein said system inspects substantially only one surface of said glass sheet.

5. The system of claim 1 wherein said system includes an enclosed chamber for receiving said illuminating means and said detecting means, and wherein said positioning means includes movable means adjacent to said enclosed chamber for moving said glass sheet into and out of a position to be surface inspected.

6. The system of claim 1 wherein said system includes imaging means for collecting said scattered ultraviolet radiation and directing said radiation to said detecting means.

7. The system of claim 6 wherein said imaging means is an ultraviolet dark field imaging system.

8. The system of claim 1 wherein said detecting means includes a charge coupled device.

9. The system of claim 1 wherein said system includes a bandpass filter for passing said ultraviolet radiation to said detecting means.

10. The system of claim 1 wherein said detecting means detects defects as small as about five microns, and wherein said processing means provides an output indicative of defects as small as about five microns.

11. An inspection system for inspecting a surface of an object, said system comprising:

an enclosed chamber:

illuminating means within said enclosed chamber for providing ultraviolet radiation within said enclosed chamber during an inspection period suitable for detecting defects substantially only at said surface of said object;

positioning means for positioning said object within said enclosed chamber for inspection and for removing said object from said enclosed chamber after inspection, said positioning means positioning said object for inspection within said enclosed chamber so that all areas of said surface to be inspected are completely illuminated by said ultraviolet radiation from said illuminating means during the entirety of said inspection period whereby defects at each said area said illuminated surface will cause scattering of said ultraviolet radiation during said inspection period;

detection means within said enclosed chamber for sensing said ultraviolet radiation scattered at each of said areas of said illuminated surface during said inspection period due to defects that are within a predetermined size range and providing an output indicative of each sensed defect; and processing means for receiving said output from said detecting means and, responsive thereto, providing an output indicative of each defect sensed at said areas of said surface of said object that is within said predetermined size range.

12. The system of claim 11 wherein said ultraviolet radiation has a dominant line of 253.7 nm.

13. The system of claim 11 wherein said object to be inspected is a sheet of flat panel glass, and wherein the surface of said glass sheet to be inspected is the front surface.

14. An inspection system for inspecting the front surface of a sheet of flat panel glass for defects, said system comprising:

an enclosed chamber;

illuminating means within said enclosed chamber for providing ultraviolet radiation within said enclosed chamber during an inspection period;

positioning means for positioning said glass sheet within said enclosed chamber for inspection and for removing said glass sheet from said enclosed chamber after inspection, said positioning means positioning said glass sheet for inspection within said enclosed chamber with said front surface to be inspected facing said illuminating means so that all areas of said front surface to be inspected are completely illuminated by said ultraviolet radiation from said illuminating means during the entirety of said inspection period whereby defects at each said area of said illuminated front surface will cause scattering of said ultraviolet radiation during said inspection period;

ultraviolet radiation dark field imaging means within said enclosed chamber for collecting ultraviolet radiation scattered at each said area of said illuminated front surface of said glass sheet within said enclosed chamber during said inspection period;

detecting means within said enclosed chamber including a charge coupled device for receiving said scattered ultraviolet radiation collected by said imaging means and providing an output indicative of each defect sensed over the entirety of said front surface that is within a predetermined size range; and processing means for receiving said output from said charge coupled device and, responsive thereto, providing an output indicative of each defect sensed at said areas of said front surface of said glass sheet that is within said predetermined size range.

15. The system of claim 14 wherein said illuminating means includes a plurality of germicidal lamps.

16. The system of claim 14 wherein said chamber is a dark field chamber.

17. The system of claim 14 wherein said chamber has shielding therein associated with said illuminating means.

18. The system of claim 14 wherein said system includes a bandpass filter centered at about 254 nm with said filter being positioned between said front surface and said imaging means.

19. The system of claim 14 wherein said system includes means for cooling said charge coupled device.

20. The system of claim 19 wherein said system includes bandpass filter means.

21. The system of claim 14 wherein said glass sheet has a size up to about 400×500 mm, and wherein said system utilizes a period of ten seconds for inspection of said front surface of said glass sheet.

22. The system of claim 21 wherein defects at least as small as five microns are detected at said front surface.

23. A method for detecting defects at a surface of a glass sheet, said method comprising:

providing ultraviolet radiation to all areas of said surface to be inspected for defects during the entirety of a predetermined inspection period whereby defects at each said area of said illuminated surface causes scattering of said ultraviolet radiation during said inspection period;

separately simultaneously detecting ultraviolet radiation scattered at said areas of said illuminated surface due to defects within a predetermined size range sensed at said areas; and using said detected ultraviolet radiation to provide an output indicative of each defect sensed at said areas of said surface that is within said predetermined size range.

24. The method of claim 23 wherein said method includes providing said ultraviolet radiation at 253.7 nm.

25. The method of claim 23 wherein said method includes providing a sheet of flat panel glass only the front surface of which is to be inspected.

26. The method of claim 25 wherein said surface to be inspected is cleaned prior to inspection to present a substantially non-degraded surface for inspection.

27. The method of claim 25 wherein said method includes illuminating the entire front surface during inspection, and detecting defects at the illuminated front surface with a charge coupled device.

28. The method of claim 27 wherein said method includes detecting defects as small as five microns using ten seconds for inspection of said front surface of said glass sheet.

* * * * *